United States Patent [19]

Poole et al.

[11] Patent Number: 4,500,432
[45] Date of Patent: Feb. 19, 1985

[54] AUTOMATED SAMPLE CONCENTRATOR FOR TRACE COMPONENTS

[75] Inventors: John S. Poole, Wilmington, Del.;
Dennis R. Gere, Westchester, Pa.;
Raymond J. Bell, Landenberg, Pa.;
Mark A. Nickerson, New London, Pa.

[73] Assignee: Hewlett-Packard Company, Palo Alto, Calif.

[21] Appl. No.: 538,832

[22] Filed: Oct. 4, 1983

Related U.S. Application Data

[63] Continuation of Ser. No. 282,482, Jul. 13, 1981, abandoned.

[51] Int. Cl.³ .............................................. B01D 15/08
[52] U.S. Cl. ...................................... 210/659; 55/67;
55/386; 210/198.2
[58] Field of Search ..................... 210/656, 659, 198.2;
55/67, 197, 386

[56] References Cited

U.S. PATENT DOCUMENTS

| | | | |
|---|---|---|---|
| 3,996,004 | 12/1976 | Fine et al. | 210/656 X |
| 4,070,284 | 1/1978 | Fujita et al. | 210/659 |
| 4,180,389 | 12/1979 | Paul | 55/67 |
| 4,311,586 | 1/1982 | Baldwin et al. | 210/198.2 |

OTHER PUBLICATIONS

Apparatus for Supercritical Fluid Chromatography with Carbon Dioxide as the Mobile Phase by Jentoft and Gouw in Analytical Chemistry, vol. 44, No. 4, Apr. 1972, pp. 681–686.
Physicochemical Principles and Applications of Supercritical Fluid Chromatography in Angewandte Chemie Int. Ed. Engl., pp. 575–587, 1980.

Primary Examiner—John Adee
Attorney, Agent, or Firm—Donald N. Timbie

[57] ABSTRACT

Concentration of the solutes contained in a liquid solvent is effected by passing the solvent through a first trapping means that adsorbs them, flushing the first trapping means with supercritical fluid and reducing its solubility parameter in a second trapping means so that the latter can adsorb desired solutes.

24 Claims, 4 Drawing Figures

AUTOMATED SAMPLE CONCENTRATOR FOR TRACE COMPONENTS

This is a continuation of application Ser. No. 282,482, filed July 13, 1981, now abandoned.

BACKGROUND OF THE INVENTION

This invention relates to method and apparatus for preparing samples of solute for introduction into instruments such as gas and liquid chromatographs that are used to measure the amounts of the solutes. In these instruments, the solutes in each sample are separated from each other by introducing the sample into a stream of carrier fluid as it enters one end of a chromatographic column. In a gas chromatograph, the carrier fluid is a gas such as nitrogen; and in a liquid chromatograph, the fluid is a liquid such as methyl alcohol. Ideally, each solute emerges from the other end of the column in the form of a separate peak having a Gaussian distribution. A detector that is coupled to the output of the column produces an electrical signal corresponding to the intensity of a given characteristic of the matter contained in each peak. The carrier fluid is selected so as to have an intensity of the given characteristic that is different from that of any of the solutes of interest in a sample. When carrier fluid alone is flowing through the detector, its output signal has what is known as a "baseline value"; and when a peak of solute is flowing through the detector, its output signal forms a corresponding peak on one side or the other of the baseline. The greater the amount of a solute in the sample, the greater is the area between the signal peak and the baseline. Thus, the amount of each solute contained in a sample can be determined by integrating the difference between the signal peak and the baseline.

Where the concentrations of the solutes of interest in the liquid solvent are sufficiently large, the sample that is introduced into the column could be taken directly from the solvent, but where there are only trace amounts of the solute of interest, the amount of a solute in such a sample may be less than the minimum detectable quantity, MDQ, required for the detector to produce a useful signal. Increasing the sample size so that each solute of interest exceeds the MDQ could cause the column to malfunction or could even destroy it. By way of example, consider measuring the amount of a solute having a concentration of one part per billion, 1 ppb, in a solvent with a flame ionization detector having an MDQ of one nanogram. In order to provide this mass of solute, one milliliter of the solvent would be required and would be 100 times larger than the largest sample size generally used of ten microliters. Therefore, the concentration of the solute must be increased by at least a factor of 100 in order to produce samples of acceptable size having solutes at least equal to the MDQ. The largest sample size that can be used is often only one microliter, thus necessitating a concentration of 1000. Even greater concentrations would be desirable in order for the detector to produce signals of higher quality.

In the past thirty-five years, ever-increasing amounts of chemicals, to which living things are highly sensitive, have been introduced into the environment by industrial and agricultural practices and have found their way into drinking water. Such chemicals as hydrocarbons, chlorinated organic solvents, pesticides and dye intermediates, as well as many others, are involved. Because of the serious consequences of even small amounts of such chemicals in drinking water and because of the effect of waste water on drinking water, federal legislation was introduced in 1973 setting forth guidelines for analyzing waste water in such a manner as to detect these chemicals when they appeared with as low a concentration as one part in a billion, 1 ppb. Even lower concentrations would be of interest, but the 1 ppb was selected because this is the best that could be done with the existing methods and, as will be described, even they have serious disadvantages.

PRIOR ART

Purge and Trap

The federal requirements for measuring solutes having a concentration of 1 ppb resulted in a Bellar and Lichtenberg, *EPA publication* 670/4-74-009, November 1974, describing the determination of volatile organic compounds at the 1 ppb level in water by the "purge and trap" preconcentration method followed by GC analysis. This technique involved placing 5 to 50 ml of water in a vessel and having a predetermined amount of inert purge gas bubbled through it. Typically 100 ml of helium or nitrogen gas was utilized. While bubbling through the water, the purge gas allows the dynamic partitioning of the "purgeable" solutes into the gas. These solutes are then carried out of the water solution by the gas and out of the initial vessel. The gas carrying the solutes then passes through a packed bed of a porous adsorbent such as "Tenax GC®", which is a polyphenoxyether polymer and a registered trademark of Enka, N.V., the Netherlands. After the prescribed quantity of solutes has been partitioned out of the water and adsorbed onto the Tenax GC® bed, the flow of gas is diverted backwards through this bed and directly onto a GC chromatographic column. This technique results in a 100 to 1000 fold preconcentration of the solutes. A limitation of this method is that only volatile, water-insoluble compounds boiling up to approximately 150° C. are effectively preconcentrated.

Liquid to a Liquid

The most common method of concentrating the solutes in a sample of water is liquid-to-liquid extraction (LLE) followed by evaporation as described in "Sampling and Analysis Procedures for Screening of Industrial Effluents for Priority Pollutants" by EPA Environmental Monitoring and Support Laboratory, Cincinnati, Ohio, April 1977. This method has the advantage of concentrating the volatile solutes not concentrated by the purge and trap method just described. In the LLE technique, a solvent such as $CH_2Cl_2$ that is immiscible with water is mixed with the water by shaking or stirring and then allowed to settle to a two-phase liquid system. The organic solutes in the water are more soluble in the immiscible organic solvent than in the water so that they "partition across" to the organic solvent during the mixing operation. The organic solvent is then manually separated from the water and the procedure repeated a number of times. The resulting organic solvent volumes containing the extracted organic solutes are then mixed together. Typically the volumes of organic solvent would be about half the volume of the water so as to produce a concentration gain of 2 if 100% of the solute "partitions across". Because this concentration gain is so small, the organic solvent is placed in an evaporative concentrator such as a "Kuderna- Danish ®" apparatus and carefully evaporated so as to reduce its volume by a factor of about 300 and thereby produce at this point a concentration gain of 600. But the final volume of the organic solvent is about 0.50 ml and therefore 50 to 500 times larger than the samples of 1 to 10 µl that are typically injected into a gas chromatograph. This means that the samples must be aliquot portions between 1/50th and 1/500th of the organic solution so as to respectively reduce the effective concentration gains to 12 and 1.2. Production of samples having solutes in excess of the MDQ from solvents having solutes with a concentration of 1 ppb requires much greater evaporation than those usually attained. Conceivably, this could be done but it would require so much time as to preclude routine analysis.

In addition to the fact that the concentration gain is too small, this liquid-to-liquid extraction technique has the following disadvantages: (1) difficult to automate; (2) different mixtures of solutes in aliquot samples; (3) accuracy depends on measurement of initial and final volumes; (4) recovery of solutes in final solvent depends on operator technique, proper solvents, surface conditions of glassware and ambient temperature stability; (5) loss of solutes during evaporation; (6) decomposition of solutes during evaporation; (7) concentration of impurities in solvent during evaporation; (8) large solvent peaks due to the organic solvent; and (9) improper operation of the detector because of organic solvent.

Junk, Fritz, et al

This method is described in *Anal. Chem.* 44, 139 (1972) and *Z. Anal. Chem.* 282, 331-337 (1976) and comprises passing large quantities of water to be analyzed through a column packed with stationary solid phase of "XAD-2 ®", a registered trademark of Rohm & Haas, Philadelphia, Pa., so as to trap out the organic solutes. A smaller volume, e.g., 25 ml of liquid such as diethyl ether, is then passed through the column so as to adsorb the solutes and produce a concentration gain of about 33. Once again, however, the final step involves evaporation in order to reduce the volume of ether down to 1 ml and provide a concentration gain of 1000. Because aliquot samples of 1 to 10 µl typically must be used in gas chromatography, which are respectively 1/1000th and 1/100th of the volume of the final ether concentrate, the effective concentration is respectively reduced to 1 and 100. Thus, only instruments using 10 µl samples can be used to analyze solvents having a 1 ppb concentration of a solute. Greater effective concentration can be obtained with greater evaporation, but this is difficult to do with accuracy. The technique has the advantage over the purge and trap method of allowing the concentration of solutes that boil in excess of 150° C., but it has nearly all of its disadvantages.

Huber Method

The concentration of trace components from liquids using high performance liquid chromatographic, HPLC, columns was discussed by Huber at the Twelfth International Symposium for Advances in Chromatography (1977) in Amsterdam, Netherlands, and published in the *Journal of Chromatography*, Vol. 142, pages 765-776 (1977). In this technique, the solvent containing the solute is pumped through an HPLC column. The organic solutes are retained by the column packing. A strong solvent for these solutes is then pumped through the column so as to cause them to elute on the "front edge" of the solvent. This "front edge" can then be selectively collected as a small "fraction", e.g., about 500 µl, and will contain most of the solutes of interest.

A concentration gain of 2000:1 can be obtained at this point without any of the problems associated with evaporation, but because the final volume of the solvent is approximately 500 µl, the samples would usually be aliquot portions with the attendant loss in effective gain. The method has the following limitations:

1. The concentration gain is limited by the minimum size front edge fraction that can be effectively collected. The limitation on fraction size is determined by the efficiency of the column and end effects due to such things as end fittings on the column and the precision and accuracy of the collection system.

2. The sample is still in a solvent matrix which must be injected into the GC for analysis. Consequently, chromatographic interferences from the solvent peak are still present.

Concentration of desired solutes by any of these methods so that each exceeds the MDQ of the detector being employed also has the disadvantage of concentrating undesired solutes so as to increase the problem of selectivity. Portions of the peaks of the undesired solutes emerging from the column and entering the detector overlap portions of peaks of the solutes of interest so that the electrical signal produced by the detector results from both a desired solute and an undesired solute, thus making it more difficult to accurately measure the area of the peak caused by the desired solute.

BRIEF DESCRIPTION OF THE INVENTION

In accordance with this invention, the liquid solvent is passed through a first trapping means such as a high performance liquid chromatographic column, HPLC, that retains solutes while permitting the solvent to pass to waste. In analyzing solutes contained in a water solvent, good results were attained with an HPLC column of 3 cm in length and having an internal diameter of 7 mm packed with "LiChrosorb ®" RP-8 with a particle diameter of 10±2 micrometers. Selectivity can be enhanced by using as the first trapping means an LC column having an appropriate stationary phase for adsorbing the desired classes of solutes while permitting undesired solutes to pass through it. The last vestiges of the solvent can be removed from the first trapping means, if desired, by passing a dry inert gas such as nitrogen through it. A further increase in selectivity can be attained by passing selected solvents through the first trapping means so as to remove undesired classes of solute from it. It is also possible for the first trapping means to include at least one more trap which may be of the same type so as to capture more of the desired solutes or it may be of a different type so as to retain at least one different class of solute.

Supercritical fluid such as supercritical $CO_2$ is then passed through the first trapping means, preferably in the opposite direction from the solvent so as to backflush it. An increase in selectivity can be attained by controlling the solubility parameter of the supercritical fluid so that its effective solvent power is adjusted to selectively carry out of the first trapping means some or all classes of desired solutes and leave undesired solutes behind. The supercritical fluid can actually include more than one supercritical gas and one or more modifiers.

The supercritical fluid that elutes from the first trapping means is then passed into a second trapping means.

The pressure and/or temperature in the second trapping means is then adjusted so that the effective solvent power of the fluid is reduced, below the effective solvent power of the super-critical fluid in the first trapping means, whether the fluid is supercritical or subcritical. The second trapping means may be comprised of a column packed with "Tenax GC ®". If all solutes are to be desorbed from the supercritical fluid, it is caused to emerge from the second trapping means in the form of a gas; but if the solutes that would be desorbed when the supercritical fluid changes into a gas from a given low pressure are not desired, this pressure is made to be the lowest pressure in the second trapping means. The change of state to a gas can then be effected outside of the trapping means. The second trapping means can be comprised of a single column or a series of columns packed with various materials so as to desorb different classes of solutes. If one column trap is used, the supercritical fluid may or may not be expelled from it in the form of a gas. When the pumping of supercritical fluid through the second trapping means ceases, the pressure on the fluid drops so that the fluid then in the second trapping means changes to a gas. At this point no desired solutes should be contained by the supercritical fluid in the second trap, but the amount of undesired solutes would be negligible, as the volume of the second trapping means with respect to the total volume of supercritical fluid passed through it is small.

In addition to producing greater concentration and having greater selectivity, this invention overcomes all of the disadvantages of the prior art previously discussed. Because all of the supercritical fluid can be made to eventually evaporate and escape in the form of gas of cryogenic temperature from the second trapping means, all the desired solutes can be left behind in a solventless form so that it is unnecessary to measure the amount of solvent in the second trapping means or to use an aliquot portion thereof as a sample. There being no solvent in the second trapping means also eliminates any concern about (1) the mixture of solutes being homogeneous, (2) the peaks produced by the solvent, or (3) the chemical changes that might result in the solutes when they are heated in the presence of a solvent.

Furthermore, the fact that the solutes are contained in the second trapping means in undiluted form makes possible a free choice of the solvents to be used so as to better prepare the sample for analysis techniques other than GC, such as LC, UV-VIS or to utilize ancillary derivitization procedures.

The high degree of effective solute concentration that is obtainable with this invention results in part from the fact that large amounts of solvent can be passed through the first trapping means and in part from the fact that the desired solutes are left in the second trapping means in solventless form. By way of example, if a detector has an MDQ of one ng of solute, only 1 ml of solvent in which the solute has a concentration of 1 ppb is required to make an analysis. Inasmuch as the first trapping means can be made to adsorb all of the solutes contained in a liter of water or other fluid, the 1 ng of solute required for a detector can be derived for solute concentrations as low as one part per trillion.

Although environmental water analysis is a natural application of this invention, it may be applied to analysis of other water-based sample matrices such as urine, serum, plasma and blood in order, for example, to measure the amounts of drugs, drug metabolites and toxicological agents that may be present therein. In the area of therapeutic drug monitoring, the matrix would be saliva, urine or plasma with a solute acetophenamin or theophylline, both traps being of the HPLC reverse bonded phase type, and the analytical device would be a high performance liquid chromatographic column followed by an ultraviolet visible detector. In the area of pharmaceuticals and drugs, the solutes, vitamins A, D and E, could be loaded onto first trapping means which is a normal phase column from a non-polar organic solvent matrix leading to a second trapping means which could also be a normal phase HPLC column, and then on to an HPLC analytical device or an analytical supercritical fluid chromatograph, sometimes called a dense gas chromatograph, DGC.

Where the matrix would be a non-polar organic solvent, preselection by a "normal phase" solid-column packing such as silica, alumina or charcoal for the first trapping means will provide retention of the anlytes followed by desorption with supercritical fluid onto the appropriate second trapping means for the chosen analytical measuring device. An example would be an extract from a foodstuff of a pesticide residue contamination dissolved in petroluem ether. A typical solute would be the pesticide methoxychlor often found in mushrooms, and the measuring device would be a gas chromatograph having an electron capture detector.

DETAILED DESCRIPTION OF AN EMBODIMENT OF THE INVENTION

Figure 1:
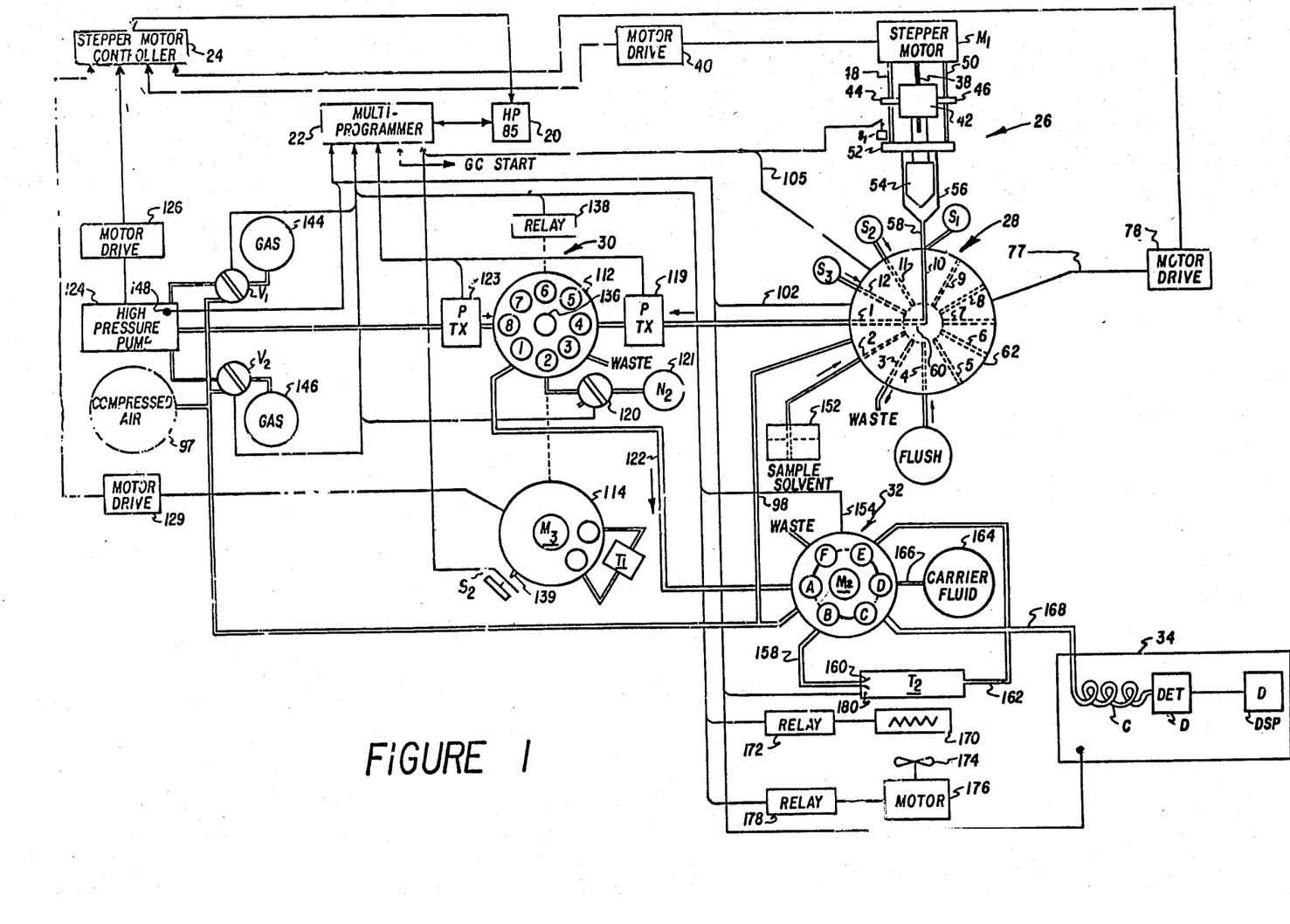
FIG. 1 is a schematic diagram of a sample concentration system that can be operated so as to concentrate sample liquids in accordance with this invention.

Reference is now made to FIG. 1 which schematically illustrates a system for concentrating the solutes of a liquid solvent in accordance with this invention. The system can be operated manually but it is preferable to operate it automatically. This can be done under the control of general purpose instruments such as a Hewlett-Packard 85 calculator 20, a Hewlett-Packard 6940A multiprogrammer 22 and a stepper motor controller 24, which may be a Compumotion 1200, as illustrated, but in a final product much saving can be accomplished by special purpose electronic controller.

In general, the system includes a syringe pump 26 for volumetrically measuring and delivering known quantities of fluid, a low pressure valve 28 for directing flow in and out of the syringe pump 26, a high pressure valve 30 that selectively positions a trap $T_1$ so as to determine whether solvent, flushing fluid or supercritical fluid is to pass through it, and a two-position valve 32 that directs supercritical fluid from a high pressure pump into a second trapping means $T_2$ while in one position and carries fluid through it and into a column C of a gas chromatograph 34 while in the other position.

In particular, the syringe pump 26 is driven by a stepper motor $M_1$ having a shaft 38 that is rotated in steps about its axis by signals from a motor drive 40 that is controlled by the stepper motor controller 24. The motor shaft 38 has a screw thread on its exterior surface that mates with threads, not shown, inside a block 42 having diametrically opposed projections 44 and 46. The projections 44 and 46 have openings, not shown, that respectively receive rods 48 and 50 with a slide fit. The rods 48 and 50 are parallel to the shaft 38 and are rigidly attached to the housing of the motor $M_1$ at one end and to a plate 52 at the other end. As the shaft 38 of the motor $M_1$ turns, the block 42 moves up or down so as to raise or lower a piston 54 that is attached to the underside of the block 42 and passes through an opening, not shown, in the plate 52. The piston 54 is contained within a cylinder 56 that is rigidly sealed to the underside of the plate 52 and has a small tube 58 extending from its lower end. The lower ends of the piston 54 and of the cylinder 56 have the same shape, preferably conical, so that when the piston 54 is in its lowest position, all of the fluid contained within the cylinder 56 is displaced into the small tube 58. A switch $s_1$ is closed by the projection 44 when the piston 54 reaches its lowest position so as to provide an appropriate signal such as a digital high voltage to the multiprogrammer 22.

Figure 1A:
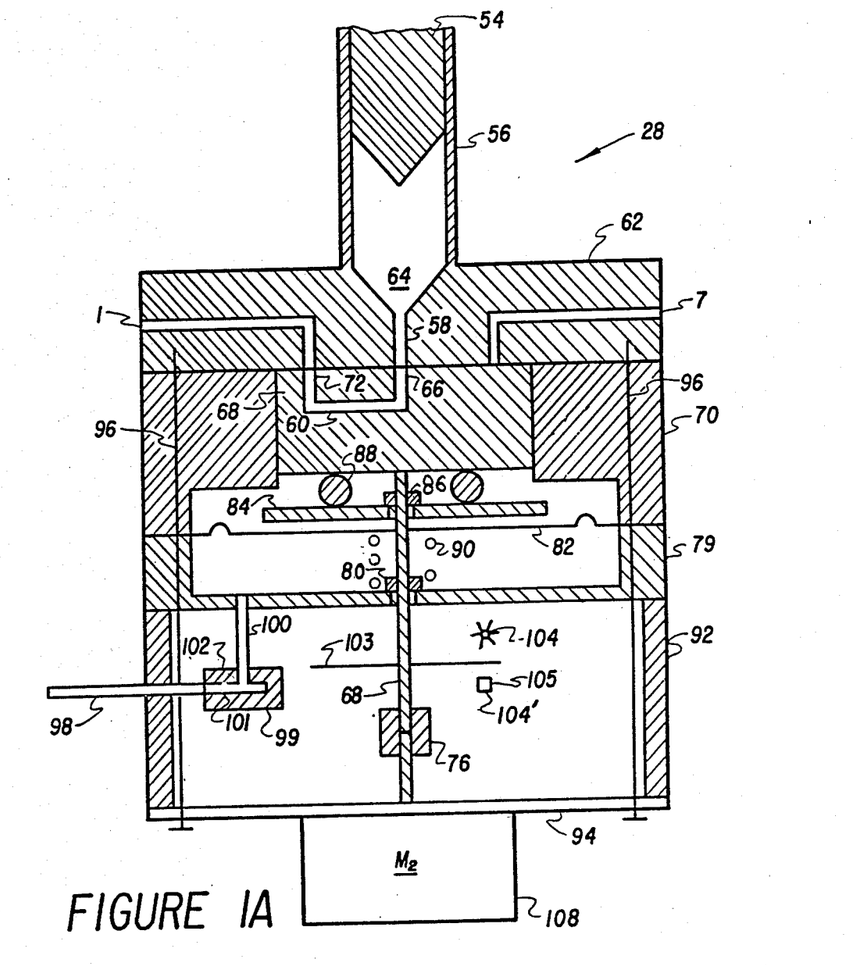
FIG. 1A is a partial cross-section of a metering valve system used in FIG. 1.
Figure 2:
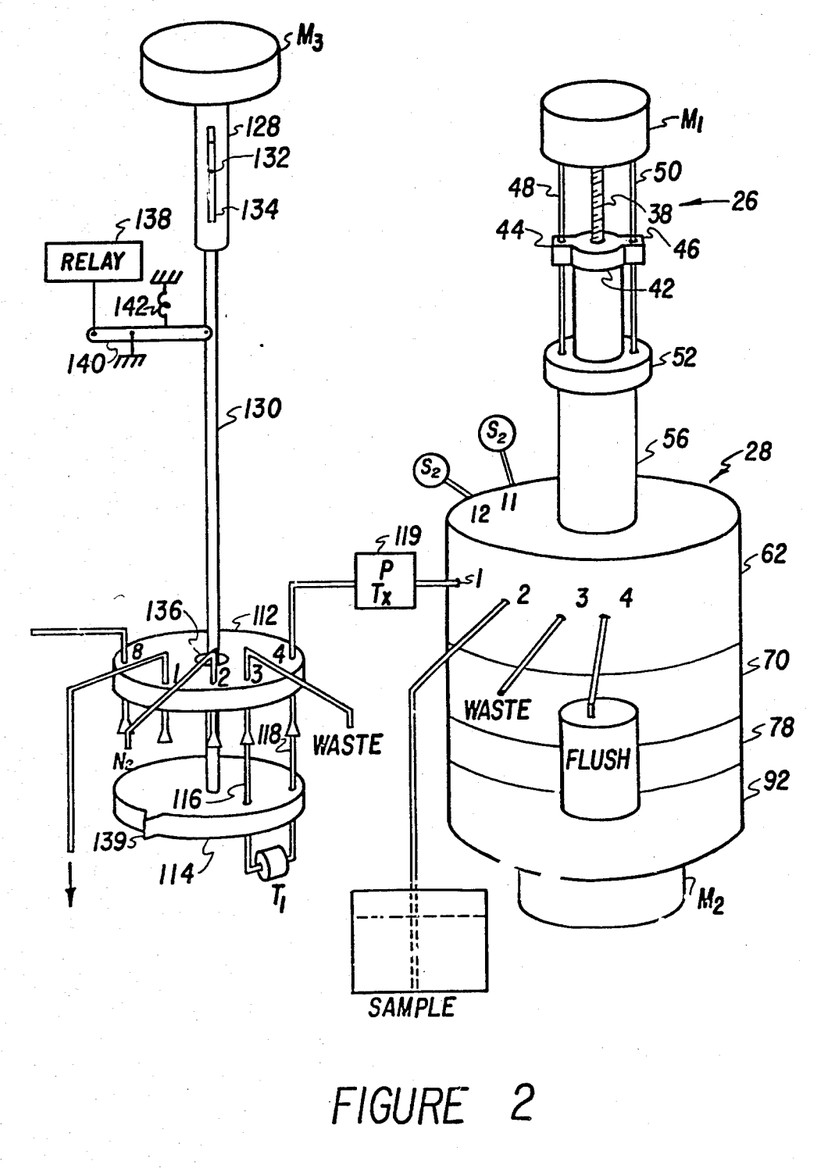
FIG. 2 is an external view of the metering valve and a high pressure valve of FIG. 1.

In the schematic top view of the valve 28 shown in FIG. 1, a passageway 60 is shown in a radial position whereby it places the tube 58 and a radial passageway 1 in communication. As will now be explained by reference to FIG. 1A, which is a vertical section of the valve 28, the passageway 60 can be rotated so as to provide communication between the tube 58 and any one of the radial passageways 1 through 12. Various electrical connections and one tube for conducting compressed air that are shown in FIG. 1A are also shown in FIG. 1 and are designated therein by the same numerals. The vertical outward appearance of the valve 28 is illustrated in FIG. 2.

In FIG. 1A, the lower end of the cylinder 56 is seen to abut a top section 62 of the body of the valve 28 with an airtight seal and to be coaxially aligned with a conical cavity 64 formed in the section 62. The tube 58, previously identified in FIG. 1, is in the form of a passageway in the section 62 that extends axially from the apex of the conical cavity 64 and communicates with a passageway 66 extending along the axis of a valve head 68 that is mounted for rotation in a section 70 of the valve 28. The passageway 66 communicates with the passageway 60, which extends along a radius of the valve head 68 and joins a vertical passageway 72 that extends to the top of the valve head 68. As illustrated by the radial passageways 1 and 7 shown in FIG. 1A, the radial passageways 1 through 12 of FIG. 1 have downwardly extending inner ends that respectively communicate with the passageway 72 when it is rotated to the correct angular position.

As just explained, the interior of the cylinder 56 can be placed in communication with any of the radial passageways 1 through 12 by rotating the valve head 68 to a suitable position. This is done by coaxially coupling the axial stem 68' of the valve head 68 to a shaft 74 of a stepping motor $M_2$, not shown in cross-section, by means of a coupler 76 that can be of any type permitting relative axial movement between the valve stem 68' and the shaft 74 but not permitting them to rotate with respect to each other. The stepping motor $M_2$ is driven by signals on a lead 77 from a motor drive unit 78 that is connected to the stepper motor controller 72 of FIG. 1.

The lower edge of the valve section 70 is in the form of a rim that mates with a similar rim on the upper side of a valve section 79 so as to form a cavity between the two sections. The bottom of the valve section 79 contains an opening for the valve stem 68' that is sealed with a seal 80. A flexible circular diaphragm 82 having a central opening for the valve stem 68' is mounted within the said cavity in a plane perpendicular to the stem 68'. Its outer periphery is clamped between the aforesaid rims, and an annular plate 84 having a central opening for the valve stem 68' is bonded to the upper surface of the diaphragm 82. The space between the valve stem 68' and the plate 84 is sealed with a seal 86 so that the portion of the cavity between the diaphragm 82 and the valve section 79 is airtight. Ball bearings 88 are mounted by any suitable means, not shown, between the plate 84 and the valve head 68, and a coiled compression spring 90 is mounted around the valve stem 68' and between the diaphragm 82 and the bottom of the valve section 79. The compression spring 90 provides sufficient force to permit the valve head 68 to be rotated with respect to the valve section 62.

An annular spacer 92 is inserted between the valve section 79 and a flange 94 of the stepping motor $M_2$. The assembly is held together by bolts 96 that pass through the flange 94, the valve sections 79 and 70, and engage threads in the valve section 62.

Figure 1B:
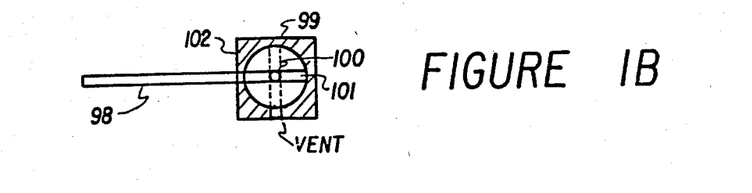
FIG. 1B is an end view of a dual position valve used in the metering valve system of FIG. 1A.

In order to prevent leakage between the passageway 72 and the one of the downwardly extending ends of the passageways 1 through 12 with which it is connected, low pressure air from a source 97 is supplied via a tube 98, see FIG. 1 and a Tee valve 99 into the space between the diaphragm 82 and the bottom of the valve section 79. This puts pressure on the diaphragm 82 and forces the top of the valve head 68 against the lower surface of the valve section 62. The Tee valve 99 is mounted with its stem 100 extending through the bottom of the valve section 79 as shown. As illustrated in FIG. 1B, the top 101 of the Tee can be connected to a source of air pressure when the Tee valve 99 is placed in one of its rotational positions by an internal relay, not shown, and to the atmosphere when the valve 99 is placed in its other rotational position by the relay. Signals for controlling the relay are conducted from the multiprogrammer 22 to the valve via a lead 102, FIG. 1.

A signal indicating the rotational position of the valve head 68 is derived in a well-known manner by mounting a disc 103 having a radial slit, not shown, for rotation with the valve stem 68' and positioning a focussed light beam source 104 on one side of the disc 103 and an electro-optical cell 104' on the other. In this particular embodiment, the light source 104 and the cell 104' are aligned so as to indicate when the passageway 72 in the valve head 68 is in communication with the radial passageway number 1. The signal produced by the cell 104' is a digital high voltage and is passed to the multiprogrammer 22 via a lead 105.

Reference is now made to the portion of FIG. 1 associated with the high pressure eight-position valve 30, the purpose of which is to place the first trapping means $T_1$ in position to have liquid solvent pass through it during one period of time and to place it in another position so that it can be backflushed with supercritical fluid during another period of time. The valve 30 will now be described by reference to its schematic representation of FIG. 1 and its physical representation in FIG. 2 taken together. The valve 30 is comprised of a stator disc 112 and a coaxial parallel rotor disc 114. Although eight valve connections respectively pass through the stator disc 112 at 45° points around a circle of a given radius, only connections 8, 1, 2 3 and 4 are used. Each valve connection extends below the stator disc 112 and terminates in a funnel. The first trapping means $T_1$ is suspended below the rotor disc 114 with its ends coupled through the disc to tubes 116 and 118 that are located so as to be able to respectively be connected to any adjacent pair of funnels of the stator valve connections.

The upper end of the valve connection 4, that is the end above the stator disc 112, is coupled via a pressure transducer 119 to the outer end of the radial tube 1 of the valve 28, the upper end of the valve connection 3 is connected to waste, the upper end of the valve connection 2 is connected via a two-position valve 120 to a source 121 of nitrogen or other inert gas, the upper end of the valve connection 1 is coupled to an inlet port A of the two-position valve 32 via a tube 122, and the upper end of the valve connection 8 is connected via a pressure transducer 123 to the output of a high pressure pump 124 which is energized by a motor drive circuit 126 under the control of signals from the motor controller 24. Although the pressure transducer 119 is not incorporated into the program presented at the end of the specification, this could be easily done. Its purpose is to reduce the speed of the syringe pump motor $M_1$ if the pressure applied to $T_1$ is too great.

Rotation of the rotor disc 114 is accomplished by a stepping motor $M_3$ which turns a hollow tube 128 that is coaxially attached to its axle, not shown. $M_3$ is energized by a driver 129 that is controlled by the stepper motor controller 24. The upper end of a rod 130 is mounted inside the tube 128 with a slide-fit and is provided with a radial projection 132 that has a slide-fit in a groove 134 extending along the length of the tube 128. The rod 130 passes through an opening 136 in the stator disc 112 with sufficient clearance to move freely therein, and its lower end is attached to the center of the rotor disc 114. When the rotor disc 114 is to be rotated, a relay 138 is energized in response to a signal from the multiprogrammer 22 so as to pull up the outer end of a lever 140 and lower the inner end as well as the rod 130 to which the inner end of the lever 140 is pivotally attached. This lowers the rotor disc 114. The ends of the tubes 116 and 118 extending upwardly from the rotor disc 114 are then sufficiently below the funnels on the lower ends of the valve connections extending below the stator disc 112 to be clear of them when they are rotated. $M_3$ is then stepped until the rotor disc 114 is rotated to the desired position and the relay 138 is de-energized so as to permit the rotor disc 114 to be moved upwardly by a spring 142 attached to the lever 140 and cause the tubes 116 and 118 to engage the funnels above them. A projection 139 is mounted on the rotor disc 114 which engages a microswitch $s_2$ mounted on the valve support bracket, not shown. When closed, the microswitch $s_2$ supplies a digital high voltage to the multiprogrammer 22 so as to indicate the rotational position to the multiprogrammer 22. The microswitch $s_2$ is positioned so as to be closed by the projection 139 when the projection 139 is aligned with position 1 on the stator disc 112.

It will be noted that there are two sources of gas for the high pressure pump 124, source 144 that is coupled to the pump via a two-position valve $V_1$, and a source 146 that is coupled to the pump via a two-position valve $V_2$. Although not shown, gas passing through the valve $V_1$ is directed so as to cool the pump body. As long as a thermometer 148 indicates to the multiprogrammer 22 that the temperature of the pump body is above 0° C., the programmer 22 sends a signal to the valve $V_1$ that causes it to open and sends a signal to the valve $V_2$ that keeps it closed. Valves $V_1$ and $V_2$ are placed in the open position by low air pressure applied to them from the source 97 of a low pressure compressed air when a digital high is applied to them and in a shut position in response to a digital low. After the temperature drops below 0° C., and if supercritical fluid is to be supplied to the high pressure valve 30, the multiprogrammer 22 causes the valve $V_2$ to open and permit gas from the source 146 to enter the pump 124. The pressure transducer 123, the multiprogrammer 22, the microprocessor 20, the stepper motor controller 24 and the motor driver 126 form a servo loop to maintain the output pressure of the pump at a desired value. As previously pointed out, the pressure can be chosen so as to cause the supercritical fluid emerging from the pump 124 to adsorb from the trap $T_1$ certain classes of solutes and not adsorb others.

Loading a sample into $T_1$ from a sample container 152 is accomplished by first placing the passageway 60 of the low pressure valve 28 in communication with the radial passageway 2 and causing the motor $M_1$ to turn in such a direction as to raise the piston 54 and draw a desired volume of sample solvent from the container 152 into the cylinder 56. Then, after the rotor disc 114 is rotated so that $T_1$ is connected between the valve connections 4 and 3, the piston 54 is lowered so as to force the solvent through the tubes 58, 66, 60, 72 and the pressure transducer 119 to the trap $T_1$. $T_1$ adsorbs the solutes and the solvent passes out to waste.

In order to backflush $T_1$ with supercritical fluid, the pump 124 is made to produce the required pressure and the rotor disc 114 of the valve 30 is rotated so as to place $T_1$ between valve connections 8 and 1. The supercritical fluid provided by the pump 124 backflushes $T_1$, carrying the solutes it adsorbs therefrom through the tube 122 to a port A of the two-position six-port valve 32 which has previously been set by a signal on a lead 154 from the multiprogrammer 22 to a position where communication is between ports connected by dotted lines, i.e., A and B, C and D, E and F. The valve 32 is actuated by low pressure air from the source 97 under the control of the signal on the lead 154 in a manner similar to the valves $V_1$ and $V_2$.

The supercritical fluid flows from port A to port B and then via a tube 158 into a second trapping means $T_2$. As it enters $T_2$ through a nozzle 160, it expands, in this particular embodiment of the invention, into a gas having a cryogenic temperature so as to release all of the solutes. They are then adsorbed by the trap $T_2$, and the gas goes via a tube 162 and ports E and F to waste.

When the amounts of the solutes are to be measured, the trap $T_2$ is reconnected between tubes 158 and 160 and the valve 32 is actuated in response to a signal on the lead 154 to a position where communication is established between ports connected by solid lines. Carrier gas from a source 164 passes through a tube 166 to port D, flows to port E and via the tube 162 to the trap $T_2$. As the carrier gas thus backflushes $T_2$, it adsorbs the solutes therefrom and carries them via the tube 158 to the port B, but port B is now connected to port C so that the carrier gas with the solutes passes through a tube 168 to the analytical instrument 34 where the solutes are quantified in any desired manner. Preferably, desorption of the solutes from the trap $T_2$ is aided by heating it, as for example with an electrical heater 170 that is turned on when a relay 172 is actuated by a signal from the multiprogrammer 22. The heating can be aided by a fan 174 that is driven by a motor 176 when a relay 178 is actuated by a signal from the multiprogrammer 22. The temperature of the trap can be kept at a desired value by turning the heater and/or fan on or off as required with a servo loop including a thermocouple 180 mounted in or on the trap $T_2$, the multiprogrammer 22, the microprocessor 20, and the relay 172. Generally, the analytical instrument 34 will have a column C for separating the solutes from each other, a detector $D_1$ and a display means DSP. An integrator may also be provided.

The nature of trap $T_2$ depends upon the medium that is to be used to transfer the solutes from the trap and the analytical instrument to be utilized. If, for example, a carrier liquid is to be used to effect the transfer, as could be the case if an HPLC is to be used for the analytical instrument, the trap $T_2$ could be an HPLC column similar to the trap $T_1$, in which case the source 164 would supply liquid. On the other hand, if a carrier gas is to be used to transfer the solutes, the trap could be a "Tenax GC®" trap and the fan F and heater H could be used for the purposes described. In all cases, special care must be taken to avoid plumbing leaks.

Instead of using a separate trap $T_2$ as the second trapping means, although this is convenient, it would be possible to use the inlet portion of either a GC, DGC or HPLC column as the trap, in which event the gas resulting from the supercritical fluid would have to pass through the analytical column.

As is well known by those skilled in the art, HPLC columns and GC columns are not mutually exclusive in their function, so that either could be used as the trap $T_1$ or the trap $T_2$. In fact, both traps $T_1$ and $T_2$ could be the same.

THE PROGRAM

The order in which various operations are done is set forth in the sequence table below, and the definition of the function to be performed is set forth in the Command Definition Table which is incorporated in the program. By way of example, the third step in the sequence table relates to the syringe pump. The "1" in the Parameter column indicates that the piston is to move upward. The 2000 in the parameter 2 column indicates that the volume is to be 2000 μl, and the parameter 3 column indicates that the rate of flow is to be 50,000 μl/min. If a different sequence of commands is to be followed, the sequence table stored in memory would be changed, and the editing means to do this is in the program. It is also possible to change the parameters for any particular command.

| Sequence Table | | | | |
|---|---|---|---|---|
| ENTRY ACTION | P1 | P2 | P3 | P4 |
| 1 LOOP | 3 | 0 | 0 | 0 |
| 2 VALVE | 2 | 2 | 0 | 0 |
| 3 SYRNG | 1 | 2000 | 50000 | 0 |
| 4 VALVE | 2 | 3 | 0 | 0 |
| 5 SYRNG | −1 | 2000 | 50000 | 0 |
| 6 VALVE | 2 | 2 | 0 | 0 |
| 7 SYRNG | 1 | 10000 | 50000 | 0 |
| 8 VALVE | 2 | 1 | 0 | 0 |
| 9 VALVE | 1 | 4 | 0 | 0 |
| 10 SYRNG | −1 | 10000 | 5000 | 0 |
| 11 VALVE | 2 | 4 | 0 | 0 |
| 12 SYRNG | 1 | 5000 | 50000 | 0 |
| 13 VALVE | 2 | 1 | 0 | 0 |
| 14 SYRNG | −1 | 5000 | 5000 | 0 |
| 15 WAIT | 5 | 0 | 0 | 0 |
| 16 VALVE | 1 | 2 | 0 | 0 |
| 17 VALVE | 4 | 1 | 0 | 0 |
| 18 WAIT | 300 | 0 | 0 | 0 |
| 19 VALVE | 4 | 0 | 0 | 0 |
| 20 VALVE | 1 | 8 | 0 | 0 |
| 21 VALVE | 3 | 1 | 0 | 0 |
| 22 PRESS | 5000 | 600 | 0 | 0 |
| 23 INJEC | 0 | 0 | 0 | 0 |
| 24 VALVE | 3 | 0 | 0 | 0 |
| 25 TEMP | 600 | 0 | 0 | 0 |
| 26 WAIT | 1800 | 0 | 0 | 0 |

| COMMAND DEFINITION TABLE | | | | |
|---|---|---|---|---|
| COMMAND | | PARAMETER 1 | PARAMETER 2 | PARAMETER 3 |
| LOOP | 1 | # OF SAMPLES | | |
| PRESS | 2 | PRESSURE IN PSI | TIME (SEC) | |
| VALVE | 3 | VALVE # | POSITION # | |
| SYRINGE | 4 | DIRECTION +1 = UP −1 = DOWN | VOLUME | FLOW RATE |
| ZONE TEMP | 5 | ZONE # | TIME ZONE ON | |
| INJECT | 6 | | | |
| WAIT | 7 | TIME (SEC) | | |
| MOVE | 8 | | | |

```
1   REM CHROMATOGRAPH INITIALIZE
5   OPTION BASE 1
6   DIM C(12),A$[50],B$[50],C$[5
    0]
7   IOBUFFER A$ @ IOBUFFER B$
8   DIM R$[33],F$[6],K$[41],D1$[
    36]
9   K$=" LOOPPRESSVALVESYRNG TEM
    PINJEC WAITSAMPL"
10  INTEGER Z(200,5),D1(12)
11  SET TIMEOUT 10;1000
12  SET TIMEOUT 7;1000
13  F$=""
14  ENABLE KBD 225
17  ON TIMEOUT 7 GOTO 9000
18  ON TIMEOUT 10 GOTO 9030
19  N=0
20  D1$="JANFEBMARAPRMAYJUNJULAU
    GSEPOCTNOVDEC"
21  FOR I=1 TO 12 @ READ D1(I)@
    NEXT I
22  DATA 31,28,31,30,31,30,31,31
    ,30,31,30,31
23  FOR I=1 TO 12 @ READ C(I)@ N
    EXT I
24  DATA 0,.024363851,5.6206931E
    -8,-3.8862562E-12
26  DATA 3.9120203E-17,0,39.4488
    72,.024548362,-9.0918433E-6
27  DATA 3923.7725,13.158,273.2
30  DISP "ENTER 24 HR TIME (HHMM
    .SS)";@ INPUT S2
31  S1=1 @ GOSUB 9650 @ IF S1=0
    THEN 30
```

```
 32  T=3600*P1+60*P2+P3
 33  DISP "ENTER DATE (MMDD,YY)"
      @ INPUT S2
 34  S1=2 @ GOSUB 9650 @ IF S1=0
      THEN 33
 35  D=0 @ FOR I=1 TO P1-1 @ D=D+
      D1(I) @ NEXT I
 36  D=P3*1000+D+P2
 37  DISP "PRESS 'CONT' TO SET TI
      ME"
 38  PAUSE
 39  SETTIME T,D @ GOSUB 9610
 40  GOSUB 7900
 90  GOSUB 200
100  ON KEY# 1,"START" GOTO 1000
110  ON KEY# 2,"LOAD"  GOTO 2000
120  ON KEY# 3,"EDIT"  GOTO 3000
130  ON KEY# 4,"DISP"  GOTO 4000
140  ON KEY# 5,"HELP"  GOTO 5000
145  ON KEY# 6,"STORE" GOTO 6000
148  ON KEY# 7,"MANUAL" GOTO 300
150  ON KEY# 8,"PRINT" GOTO 4800
160  CLEAR @ KEY LABEL
170  GOTO 170
200  OFF KEY# 1
210  OFF KEY# 2
220  OFF KEY# 3
230  OFF KEY# 4
240  OFF KEY# 5
250  OFF KEY# 6
260  OFF KEY# 7
270  OFF KEY# 8
280  RETURN
300  GOSUB 1500
310  GOTO 90
1000 GOSUB 1150
1050 P=0 @ Q=0 @ W=0 @ W1=0
1055 IF N=0 THEN DISP "NO TABLE
      ENTRIES" @ GOTO 1110
1056 IF W=1 THEN DISP "RUN PAUSE
      D AT LINE ",P+1
1058 IF W=1 THEN 1058
1061 P=P+1 @ IF P<=N THEN 1067
1062 IF Q=0 THEN 1300
1064 Q=Q+1 @ IF Q>Z(O1-1,2) THEN
      1300
1066 P=Q1 @ GOSUB 9600
1067 CLEAR @ DISP "LINE #";P @ K
      EY LABEL
1068 ON Z(P,1) GOSUB 8000,8100,8
      200,8300,8400,8500,8600,870
      0
1070 IF W1=1 THEN W=1 @ DISP "SI
      NGLE STEP AT LINE ";P+1 @ G
      OTO 1058
1075 GOTO 1056
1100 GOSUB 7980
1105 C$="Z " @ GOSUB 7300
1108 DISP "RUN ABORTED!"
1110 BEEP
1115 WAIT 500
1120 GOTO 90
1150 GOSUB 200
1155 ON KEY# 1,"ABORT" GOTO 1100
1160 ON KEY# 2,"PAUSE" GOSUB 120
      0
1165 ON KEY# 3,"RESUME" GOSUB 12
      40
1170 ON KEY# 4,"NEXT" GOSUB 1280
1172 ON KEY# 6,"SKIP" GOSUB 1380
1174 ON KEY# 7,"MANUAL" GOSUB 13
      50
1175 CLEAR @ KEY LABEL
1180 RETURN
1200 W=1 @ W1=0
1210 RETURN
1240 W=0 @ W1=0
1250 RETURN
1280 W=0 @ W1=1
1290 RETURN
1300 DISP "RUN OVER" @ GOTO 1110
1350 IF W=0 AND W1=0 THEN RETURN
1355 GOSUB 1500
1360 GOSUB 1150
1370 RETURN
1380 IF W=0 AND W1=0 THEN RETURN
1385 DISP "SKIPPING LINE",P+1
1388 P=P+1
1390 RETURN
1400 GOSUB 7900
1410 GOTO 1500
1420 GOSUB 7940
1430 GOTO 1500
1440 GOSUB 7950 @ GOTO 1500
1460 GOSUB 7700 @ GOTO 1500
1480 GOSUB 7980 @ GOTO 1500
1490 RETURN
1500 GOSUB 200
1510 ON KEY# 1,"NORMAL" GOTO 149
      0
1520 ON KEY# 2,"STEP" GOTO 1600
1530 ON KEY# 3,"INITIAL" GOTO 18
      00
1540 ON KEY# 4,"SHOW" GOTO 1900
1545 ON KEY# 5,"HELP" GOTO 1950
1550 ON KEY# 6,"RELAYS" GOTO 170
      0
1590 CLEAR @ KEY LABEL
1595 GOTO 1595
1600 CLEAR
1610 O=200
1620 GOSUB 9300
1625 P1=200 @ P2=200
1630 GOSUB 9400
1635 DISP "O K ",
1640 GOSUB 9200
1645 IF R=1 THEN 1670
1650 DISP "CHANGE";
1655 GOSUB 9200
1660 IF R=0 THEN 1590 ELSE 1600
1670 P=200
1680 ON Z(P,1) GOSUB 8000,8100,8
      200,8300,8400,8500,8600,870
      0
1685 GOTO 1590
1700 CLEAR @ DISP "SELECT OPTION
      "
1710 DISP "1=CO2 COOLING    7=UNA
      SSIGNED"
1720 DISP "2=CO2 SUPPLY     8=SYR
      INGE ROTOR"
1725 DISP "3=UNASSIGNED     9=NIT
      ROGEN"
1730 DISP "4=SAMPLER       10=TRA
      P COOLING"
1735 DISP "5=COLUMN ROTOR  11=COL
      UMN HEAT"
1740 DISP "6=UNASSIGNED    12=TRA
      P HEAT";
1750 INPUT T@ T=INT(T)
1755 IF T<1 OR T>12 THEN 1700
1758 S1=2^(T-1) @ S2=1
1760 DISP "1=ON, 0=OFF";
1765 INPUT T@ T=INT(T)
1770 IF BIT(T,0) THEN GOSUB 7200
      ELSE GOSUB 7250
```

```
1775 GOTO 1590
1800 GOSUB 200
1810 ON KEY# 1,"ALL" GOTO 1400
1820 ON KEY# 2,"VALVE 1" GOTO 14
     20
1830 ON KEY# 3,"VALVE 2" GOTO 14
     40
1840 ON KEY# 4,"SYRINGE" GOTO 14
     60
1860 ON KEY# 6,"I/O" GOTO 1480
1870 CLEAR @ KEY LABEL
1875 GOTO 1875
1900 CLEAR @ KEY LABEL
1910 DISP "VALVE 1 POSITION ";R1
1920 DISP "VALVE 2 POSITION ";R2
1930 DISP "SYRINGE VOLUME   ";V
1940 GOTO 1595
1950 CLEAR @ KEY LABEL
1952 DISP
1955 DISP "KEY 1 _ ALLOWS NORMAL
      OPERATION"
1958 DISP "KEY 2 - SINGLE STEP M
     ODE"
1960 DISP "KEY 3 - RE-INITIALIZE
     S SYSTEM"
1962 DISP "KEY 4 - DISPLAYS VALV
     E POSITION"
1965 DISP "KEY 5 - HELP"
1968 DISP "KEY 6 - ALLOWS RELAY
     CONTROL"
1975 GOTO 1595
2000 DISP "FILE NAME";
2010 INPUT F$
2015 IF F$="" THEN OFF ERROR @ G
     OTO 160
2020 ON ERROR GOTO 2000
2030 ASSIGN# 1 TO F$
2040 READ# 1 ; N,Z(,)
2050 OFF ERROR
2060 DISP "DONE"
2070 GOTO 160
3000 GOSUB 200
3010 ON KEY# 1,"EXIT" GOTO 90
3020 ON KEY# 2,"ADD" GOTO 3200
3030 ON KEY# 3,"DELETE" GOTO 330
     0
3040 ON KEY# 4,"DISP" GOTO 3400
3050 ON KEY# 5,"HELP" GOTO 3500
3060 ON KEY# 6,"INSERT" GOTO 360
     0
3070 ON KEY# 7,"CHANGE" GOTO 370
     0
3080 ON KEY# 8,"PRINT" GOTO 3800
3090 CLEAR
3095 KEY LABEL
3100 GOTO 3100
3160 BEEP @ DISP "TABLE FULL" @
     GOTO 3095
3180 BEEP @ DISP "TABLE EMPTY" @
     GOTO 3095
3190 CLEAR @ BEEP @ DISP "NOT IN
     TABLE" @ GOTO 3095
3200 IF N>199 THEN 3160
3202 N=N+1
3204 CLEAR
3206 DISP "ADDING LINE ";N
3210 Q=N
3220 GOSUB 9300
3275 DISP "ANOTHER ENTRY"
3280 GOSUB 9200
3285 IF R=0 THEN 3000
3290 GOTO 3200
3300 IF N=0 THEN 3180
3303 CLEAR @ DISP "DELETE ENTRIE
     S FROM, TO";
3305 INPUT P1,P2@ P1=INT(P1) @ P
     2=INT(P2)
3310 IF P1=0 AND P2=0 THEN 3370
3314 IF P1>P2 THEN 3303
3315 IF P1<1 THEN 3095
3316 IF P2>N THEN P2=N
3325 P3=P2-P1+1
3328 N=N-P3
3330 FOR J=P1 TO N
3335 FOR I=1 TO 5
3340 Z(J,I)=Z(J+P3,I)
3345 NEXT I
3350 NEXT J
3365 GOTO 3090
3370 DISP "DELETE ENTIRE TABLE";
3375 GOSUB 9200
3380 IF R=1 THEN N=0 @ GOTO 3180
3385 GOTO 3090
3400 IF N=0 THEN 3180
3410 GOSUB 9500
3420 GOTO 3090
3500 CLEAR @ KEY LABEL
3505 DISP "KEY 1 - LEAVES EDIT M
     ODE"
3510 DISP "KEY 2 _ ADDS NEW TABL
     E ENTRIES"
3520 DISP "KEY 3 - DELETES TABLE
      ENTRIES"
3530 DISP "KEY 4 - DISPLAYS TABL
     E ENTRIES"
3540 DISP "KEY 5 - HELP"
3550 DISP "KEY 6 - INSERTS A TAB
     LE ENTRY"
3560 DISP "KEY 7 - CHANGES A TAB
     LE ENTRY"
3570 DISP "KEY 8 - PRINTS TABLE
     ENTRIES"
3580 GOTO 3100
3600 IF N>200 THEN 3160
3605 CLEAR
3610 DISP "INSERT BEFORE ENTRY #
     ";@ INPUT T
3615 T=INT(T)
3620 IF T<1 THEN 3000
3625 IF T>N THEN 3190
3630 N=N+1
3645 FOR J=N TO T+1 STEP -1
3648 FOR I=1 TO 5
3650 Z(J,I)=Z(J-1,I)
3652 NEXT I
3655 NEXT J
3660 Q=T
3685 GOSUB 9300
3690 GOTO 3000
3700 CLEAR
3710 DISP "ENTRY TO BE CHANGED";
3720 INPUT T@ T=INT(T)
3730 IF T<1 THEN 3090
3735 IF T>N THEN 3190
3740 P1=T @ P2=T
3750 GOSUB 9410
3755 Q=T
3760 GOSUB 9300
3770 GOTO 3000
3800 IF N=0 THEN 3180
3820 GOSUB 9700
3830 GOTO 3090
4000 IF N=0 THEN 4100
4010 GOSUB 9500
4020 GOTO 160
4100 BEEP @ DISP "TABLE EMPTY" @
     GOTO 170
```

```
4800 IF N=0 THEN 4100
4805 PRINT F$
4810 GOSUB 9610
4820 GOSUB 9700
4850 GOTO 160
5000 CLEAR @ KEY LABEL
5005 DISP
5010 DISP "KEY 1 _ STARTS RUN"
5015 DISP "KEY 2 - LOADS RUN TAB
      LE FROM"
5018 DISP "           TAPE"
5020 DISP "KEY 3 - EDITS RUN TAB
      LE"
5030 DISP "KEY 4 - DISPLAYS RUN
      TABLE"
5040 DISP "KEY 5 - HELP"
5050 DISP "KEY 6 - STORES RUN TA
      BLE ON TAPE"
5055 DISP "KEY 7 - ALLOWS MANUAL
       OPERATION"
5060 DISP "KEY 8 - PRINTS RUN TA
      BLE"
5090 GOTO 170
6000 IF N=0 THEN 4100
6010 ON ERROR GOTO 6020
6020 DISP "FILE NAME";
6030 INPUT F$
6035 IF F$="" THEN OFF ERROR @ G
     OTO 160
6040 DISP "CREATE FILE";
6050 GOSUB 9200
6060 IF P=1 THEN CREATE F$ 33
6070 ASSIGN# 1 TO F$
6080 PRINT# 1 ; N,Z(*)
6085 ASSIGN# 1 TO *
6090 GOTO 2050
7000 REM RELAY READBACK
7005 OUTPUT 723 ;"00240T"
7010 OUTPUT 723 ;CHR$(64+S2)&"X"
7020 ENTER 723 ; X$
7030 S3=OTD(X$)-4096
7035 RETURN
7039 REM RELAY WRITE
7040 OUTPUT 723 ;"00140T"&CHR$(6
     4+S2)&OTD$(S3)&"T"
7045 RETURN
7100 REM READ HI LEVEL ADC
7120 OUTPUT 723 ;"00240T@T@X"
7130 ENTER 723 ; X$
7140 X=8192-OTD(X$)
7150 RETURN
7200 REM TURN ON RELAY(S)
7210 GOSUB 7000
7220 S3=BINIOR(S3,S1)
7230 GOSUB 7040
7240 RETURN
7250 REM TURN OFF RELAY(S)
7260 GOSUB 7000
7270 S3=BINAND(S3,BINCMP(S1))
7280 GOSUB 7040
7290 RETURN
7300 A$=C$
7310 B$=""
7320 GOSUB 7400
7325 RETURN
7350 C$="1P"
7360 GOSUB 7500
7365 RETURN
7400 TRANSFER A$ TO 10 INTR
7410 TRANSFER 10 TO B$ INTR ; DE
     LIM 13
7420 RETURN
7450 STATUS B$,2 ; T2
7455 IF T2#0 THEN 7450
7460 RETURN
7500 A$=C$ @ B$=""
7510 GOSUB 7400
7515 GOSUB 7450
7520 B$=""
7525 GOSUB 7410
7530 GOSUB 7450
7535 D$=B$[1,LEN(B$)-1]
7540 RETURN
7550 C$="1R" ! CHECK MOTOR STATU
     S
7560 GOSUB 7500 @ IF D$#"R" THEN
      7560
7575 RETURN
7600 REM INITIALIZE ROTORS
7602 DISP "INITIALIZING VALVE #"
     ;S4+1
7605 OUTPUT 723 ;"00240T"
7610 GOSUB 7690
7615 IF BIT(X,S4) THEN RETURN
7618 ON TIMER# 1,40000 GOTO 9050
7620 GOSUB 7200 @ WAIT 500
7625 C$="E V 1 A10 MC H+ "&D$&"
     G"
7630 GOSUB 7300 @ C$="S "
7640 GOSUB 7690
7645 IF BIT(X,S4) THEN 7647 ELSE
      7640
7647 OFF TIMER# 1 @ J=-5 @ GOSUB
      7300
7648 IF J=-5 THEN K=1 @ C$="MN D
     -.003 V1 G"
7649 IF J=5 THEN K=-1 @ C$="MN D
     +.003 V1 G"
7650 J=J+K
7651 WAIT 500
7652 GOSUB 7300
7654 GOSUB 7690
7656 IF BIT(X,S4) THEN 7672
7660 GOTO 7648
7672 GOSUB 7250 @ WAIT 500
7675 RETURN
7690 OUTPUT 723 ;"DX"
7692 ENTER 723 ; X$
7694 X=OTD(X$)
7696 RETURN
7700 DISP "INITIALIZING SYRINGE
     PUMP"
7702 V=0
7705 OUTPUT 723 ;"00240T"
7710 GOSUB 7690
7715 IF BIT(X,2) THEN RETURN
7720 C$="E V.5 A10 MC H- XH G"
7725 GOSUB 7300 @ C$="S "
7730 GOSUB 7690
7735 IF BIT(X,2) THEN 7740 ELSE
     7730
7740 GOSUB 7300
7745 C$="MN D-.3 G"
7750 GOSUB 7300
7755 RETURN
7900 GOSUB 7980
7910 CLEAR
7915 GOSUB 7940
7920 GOSUB 7950
7925 GOSUB 7700
7930 RETURN
7940 S1=16 @ S4=0 @ D$="XA" @ S2
     =1 @ R1=1
7945 GOSUB 7600
7948 RETURN
7950 S1=128 @ S4=1 @ D$="XB" @ S
     2=1 @ R2=1
7955 GOSUB 7600
```

```
7958 RETURN
7980 RESET 10 @ RESET 7
7982 CONTROL 10,6 ; 0.12 ! BAUD
     RATE
7984 CONTROL 10,4 ; 14 ! PARITY
7986 CONTROL 10,16 ; 1 ! DELIM
7988 X=SPOLL(723)
7990 OUTPUT 723 ;"0160TA0TC0T014
     0T"
7992 RETURN
8000 IF Z(P,2)<1 THEN 1300
8010 Q=1
8020 Q1=P+1
8025 GOSUB 9600
8030 RETURN
8100 F1=1 @ Y=0 @ F=20 @ G=.01 @
      G2=.001 @ V1=0 @ V2=0 @ W2
     =0
8104 S1=2 @ S2=1 @ GOSUB 7200 !
     TURN ON CO2
8105 S1=1024 @ S2=1 @ GOSUB 7200
      ! TURN ON COL HEAT
8106 S1=1 @ S2=3 @ GOSUB 7200 !
     TURN ON ADC
8107 S1=1 @ S2=1
8108 C$="E XD MC A10 H+" @ P1=Z(
     P,2) @ GOSUB 7300
8110 P2=Z(P,3)*1000
8111 ON TIMER# 1,300000 GOTO 915
     0
8112 IF W2=1 THEN 8191
8113 GOSUB 7100 @ Y=Y+1 @ CLEAR
8114 X=3.5586*X @ DISP INT(X),IN
     T(F*10)/10
8115 IF X>7000 THEN 9150
8116 ON Y GOTO 8120,8130,8140
8120 OUTPUT 723 ;"0160TB7T0260T"
8121 OUTPUT 723 ;"BX" @ ENTER 72
     3 ; X$
8122 R=(OTD(X$)-4096)*10/4352
8123 R=C(10)/(C(11)+LOG(-R))-C(1
     2)
8124 R=R*(C(7)+R*(C(8)+R*C(9)))*
     .000001
8126 GOTO 8144
8130 OUTPUT 723 ;"0160TB1T0260T"
     @ OUTPUT 723 ;"BX"
8132 ENTER 723 ; X$
8134 T=OTD(X$)
8136 T=(T-(T>2047)*4096)*.00001
8138 T=(R+T)*1000000 @ GOTO 8144
8140 F=C(1)+T*(C(2)+T*(C(3)+T*(C
     (4)+T*C(5))))
8142 Y=0
8144 IF F>1 THEN 8170
8145 IF X<F1 THEN 8150
8146 IF P2>0 THEN OFF TIMER# 1 @
      ON TIMER# 1,P2 GOSUB 8190
     @ P2=0
8150 E=P1-X
8152 IF ABS(E)/P1<.05 THEN V2=V2
     +G2*E @ V1=G*E+V2 ELSE V1=G
     *E @ V2=0
8154 IF V1<0 THEN V1=0
8156 IF V1>5 THEN V1=5
8158 C$="V"&VAL$(INT(V1*1000)/10
     00)&" G"
8160 GOSUB 7300
8170 IF F>3 THEN 8130
8174 IF F<0 THEN 8185
8176 F1=F1-1
8178 IF F1>=0 THEN 8185
8180 GOSUB 7200 @ F1=1
8182 GOTO 8112
8185 GOSUB 7250
8188 GOTO 8112
8190 OFF TIMER# 1 @ W2=1 @ RETUR
     N
8191 S1=1 @ S2=1 @ GOSUB 7250
8192 S1=2 @ S2=1 @ GOSUB 7250
8193 S1=1024 @ S2=1 @ GOSUB 7250
8195 C$="S " @ GOSUB 7300
8197 S1=1 @ S2=3 @ GOSUB 7250
8198 RETURN
8200 P2=Z(P,3) @ ON Z(P,2) GOTO
     8205,8240,8280,8286
8205 P3=P2-R1 @ IF P3=0 THEN RET
     URN
8210 S1=16 @ S2=1 @ GOSUB 7200 @
      WAIT 500
8215 P1=8 @ GOSUB 8290 @ R1=P2
8220 C$="E XA MN A10 V1 D"&VAL$(
     D)&" G" ! MOVE VALVE
8225 GOSUB 7300
8228 GOSUB 7550
8230 GOSUB 7250 @ WAIT 500
8235 RETURN
8240 P3=P2-R2 @ IF P3=0 THEN RET
     URN
8245 S1=128 @ S2=1 @ GOSUB 7200
     @ WAIT 500
8250 P1=12 @ GOSUB 8290 @ R2=P2
8255 C$="E XB MN A10 V2 D"&VAL$(
     D)&" G" ! MOVE VALVE
8260 GOSUB 7300
8270 GOSUB 7550
8272 IF R2=1 THEN S4=1 @ D$="XB"
      @ GOSUB 7605
8275 GOSUB 7250 @ WAIT 500
8276 RETURN
8280 S1=32 @ S2=1
8282 IF BIT(Z(P,3),0) THEN GOSUB
      7200 ELSE GOSUB 7250
8284 RETURN
8286 S1=256 @ S2=1 @ GOTO 8282
8290 IF P3<0 THEN P3=P3+P1
8291 IF P3>P1/2 THEN P3=-P1+P3
8292 D=-(INT(2040*P3/P1)/1000)
8295 RETURN
8300 IF Z(P,5)#0 THEN 8380
8301 V1=INT(Z(P,4)*.0166667)*.00
     204
8302 IF Z(P,2)<0 THEN V=V-Z(P,3)
      ELSE V=V+Z(P,3)
8304 IF V<0 THEN 9110
8310 D=INT(Z(P,3)*2.04)/1000
8315 S1=2 @ S2=3 @ GOSUB 7200
8320 IF Z(P,2)<0 THEN D=-D
8340 C$="E XH MN A10 D"&VAL$(D)&
     " V"&VAL$(V1)&" G"
8341 GOSUB 7300
8342 OUTPUT 723 ;"0024OT"
8347 GOSUB 7690
8348 IF BIT(X,3) THEN 9106
8350 GOSUB 7100
8351 IF X>141 THEN 8368
8352 C$="1R"
8355 GOSUB 7500 @ IF D$#"R" THEN
      8347
8362 S1=2 @ S2=3 @ GOSUB 7250
8365 RETURN
8368 V1=V1*.9 @ BEEP
8369 PRINT "SYRINGE OVER-PRESSUR
     E"
8370 ON ERROR GOTO 9900
8371 C$="S " @ GOSUB 7300
8372 GOSUB 7550
8374 GOSUB 7350
```

```
8376 D=D-VAL(D$)
8377 Z(P,4)=Z(P,4)*.9 @ PRINT "N
     EW FLOW RATE";Z(P,4);"uL/MI
     N"
8378 GOTO 8340
8380 C$="E XH H- MC A10 V 05 G"
8382 ON TIMER# 1,60000 GOTO 9130
8383 OUTPUT 723 ;"00240T"
8384 GOSUB 7300
8386 GOSUB 7690
8388 IF BIT(X,5) THEN 8386
8390 C$="S " @ GOSUB 7300
8392 GOSUB 7550
8394 OFF TIMER# 1
8395 GOTO 8301
8400 REM TURN ON TRAP HEAT
8405 S1=2048 @ S2=1
8410 GOSUB 7200
8415 ON TIMER# 3,Z(P,2)*1000 GOS
     UB 8440 ! TURN OFF HEATER
8420 RETURN
8440 OFF TIMER# 3
8445 S1=2048 @ S2=1
8450 GOSUB 7250
8455 S1=512 @ S2=1 @ GOSUB 7200
8460 ON TIMER# 3,300000 GOSUB 84
     70
8465 RETURN
8468 REM TURN ON COOLING FAN
8470 S1=512 @ S2=1 @ GOSUB 7250
8475 OFF TIMER# 3
8480 RETURN
8500 S1=64 @ S2=3
8510 GOSUB 7200
8520 WAIT 1000
8530 GOSUB 7250
8540 RETURN
8600 FOR J=1 TO Z(P,2)
8610 FOR I=1 TO 556
8620 NEXT I
8630 NEXT J
8640 RETURN
8700 S1=8 @ S2=1
8710 IF Z(P,2)#0 THEN GOSUB 7200
     @ RETURN
8720 GOSUB 7250 @ WAIT 1000
8725 GOSUB 7200 @ WAIT 1000
8730 GOSUB 7250 @ RETURN
9000 CLEAR
9005 DISP "HPIB INTERFACE FAILUR
     E"
9010 GOTO 9030
9020 CLEAR
9025 DISP "SERIAL INTERFACE FAIL
     URE"
9030 BEEP @ BEEP @ BEEP
9040 DISP "PRESS 'CONT' TO CONTI
     NUE"
9045 PAUSE
9048 GOTO 90
9050 OFF TIMER# 1 @ DISP "INDEXI
     NG FAILURE"
9055 C$="S "
9060 GOSUB 7300
9065 GOTO 9030
9080 C$="K"
9085 GOSUB 7300
9090 RETURN
9100 OFF TIMER# 1
9105 GOSUB 9080
9110 DISP "SYRINGE PUMP VOLUME E
     RROR"
9120 GOTO 9030
9130 DISP "FRACTION COLLECTOR PR
     OBLEM" @ OFF TIMER# 1 @ GOT
     O 9030
9150 DISP "PUMP-PRESSURE PROBLEM
     " @ OFF TIMER# 1 @ GOSUB 79
     80
9160 GOTO 9030
9200 P=0
9210 INPUT R$
9215 IF UPC$(R$[1,1])="Y" THEN P
     =1
9220 RETURN
9240 INPUT T
9242 T=INT(T)
9244 Z(Q,I)=T
9245 I=I+1
9246 RETURN
9300 FOR I=2 TO 5 @ Z(Q,I)=0 @ N
     EXT I
9302 DISP "FUNCTION"
9304 DISP "   1=REPEAT"
9306 DISP "   2=PUMP PRESS"
9308 DISP "   3=VALVE POSITION"
9310 DISP "   4=SYRINGE PUMP"
9312 DISP "   5=ZONE TEMP"
9314 DISP "   6=INJECT"
9316 DISP "   7=WAIT"
9318 DISP "   8=SAMPLE"
9320 I=2 @ INPUT T@ T=INT(T)
9322 IF T<1 OR T>8 THEN 9302
9323 Z(Q,1)=T
9324 ON T GOTO 9362,9326,9332,93
     41,9327,9348,9327,9392
9326 DISP "PRESSURE";@ GOSUB 924
     0
9327 DISP "TIME (IN SEC)" @ GOSU
     B 9240
9328 RETURN
9332 DISP "VALVE #";
9334 GOSUB 9240
9336 DISP "POSITION";
9337 GOSUB 9240
9338 RETURN
9341 DISP "DIRECTION (-1=DOWN, 1
     =UP)";
9342 GOSUB 9240
9344 DISP "VOLUME (IN uL)";
9345 GOSUB 9240
9346 DISP "FLOW RATE (IN uL/MIN)
     ";
9347 GOSUB 9240
9348 DISP "FRACTION COLLECT? (1=
     YES, 0=NO)";
9349 GOSUB 9240
9350 RETURN
9362 DISP "# OF REPETITIONS ";
9364 GOSUB 9240
9366 RETURN
9392 DISP "SAMPLE (1=GET, 0=PUT
     BACK"
9394 GOSUB 9240
9395 RETURN
9400 CLEAR
9410 DISP "ENTRY ACTION  P1   P2
            P3   P4"
9415 FOR I=P1 TO P2
9416 S1=Z(I,1)*5-5
9417 C$=K$[S1+1,S1+5]
9420 DISP USING 9490 ; I,C$,Z(I,
     2),Z(I,3),Z(I,4),Z(I,5)
9422 NEXT I
9425 RETURN
9490 IMAGE 3D,X,5A,X,5D,X,5D,X,5
     D,X,4D
```

```
9500 P1=1 @ P2=12 @ P3=0
9510 IF P2>=N THEN P2=N @ P3=1
9520 CLEAR
9530 GOSUB 9400
9540 DISP "PRESS 'CONT' TO CONTI
     NUE"
9550 PAUSE
9560 P1=P1+12 @ P2=P2+12
9570 IF P3=0 THEN 9510
9580 RETURN
9600 PRINT "RUN #";
9610 D=DATE @ T=INT(TIME)
9615 P1=INT(D/1000)+1900
9620 P2=INT(FP(D/1000)*1000)
9625 IF P2>365 THEN P2=P2-365 @
     D=(P1-1899)*1000+P2 @ SETTI
     ME TIME,D @ P1=P1+1
9628 FOR I=1 TO 12
9629 P2=P2-D1(I)
9630 IF P2<=0 THEN P2=P2+D1(I) @
      P3=I-1 @ I=13
9632 NEXT I
9636 P4=T\3600
9637 T=T MOD 3600
9638 P5=T\60
9639 P6=T MOD 60
9642 PRINT USING 9690 ; P4,P5,P6
     ,D1$[P3*3+1,P3*3+3],P2,P1
9644 PRINT @ PRINT
9645 RETURN
9650 P1=INT(S2/100)
9652 P2=INT(S2-P1*100)
9654 P3=INT(FP(S2)*100)
9656 ON S1 GOTO 9660,9670
9660 IF P1<0 OR P1>23 THEN 9680
9662 IF P2<0 OR P2>59 THEN 9680
9664 IF P3<0 OR P3>59 THEN 9680
9666 RETURN
9670 IF P1<1 OR P1>12 THEN 9680
9672 IF P2<1 OR P2>D1(P1) THEN 9
     680
9676 RETURN
9680 S1=0 @ RETURN
9690 IMAGE 2D,":",2Z,":",2Z,2X,3
     A,X,2D,". ",4D
9700 CRT IS 2
9715 P1=1 @ P2=N
9720 GOSUB 9400
9725 CRT IS 1
9728 PRINT USING "5/"
9730 RETURN
9900 STATUS A$,0 ; T0,T1,T2,T3
9910 DISP T0,T1,T2,T3
9920 STATUS B$,0 ; T0,T1,T2,T3
9930 DISP T0,T1,T2,T3
9940 DISP A$
9950 DISP B$
9960 DISP C$
9970 DISP D$
9980 OFF ERROR
9999 END !  1JUN81   R BELL
```

What is claimed is:

1. A method of concentrating solutes contained in a liquid solvent other than supercritical fluid before they are applied to chromatographic apparatus for analysis, the said method comprising:

passing the liquid solvent to waste through a first trapping means that adsorbs and accumulates at least some of the solutes from the solvent, passing supercritical fluid through said first trapping means so as to adsorb at least some of the solutes therefrom and carry them into a second trapping means, reducing the solubility parameter of the supercritical fluid in said second trapping means, and permitting the fluid of reduced solubility parameter to escape from said second trapping means, thereby leaving at least some of the solutes in said second trapping means.

2. Apparatus for concentrating the solutes contained in a liquid solvent other than supercritical fluid before they are applied to chromatographic apparatus for analysis, comprising:

a first trapping means containing material for adsorbing and accumulating at least some solutes from said liquid solvent other than supercritical fluid passing through it, means for causing the liquid solvent, when present, to flow through said first trapping means and out to waste, second trapping means, means for changing a liquid-gas combination into supercritical fluid and to cause said supercritical fluid to flow through said first trapping means and into said second trapping means, said means for changing a liquid-gas combination into supercritical fluid being operative when a source of liquid-gas is coupled thereto, said second trapping means being such as to reduce the density of any supercritical fluid entering it so as to reduce its solubility parameter and thus retain at least some of the solutes.

3. Apparatus as set forth in claim 2 wherein said first trapping means is of the reverse phase type.

4. Apparatus as set forth in claim 3 wherein said second trapping means contains polyphenoxy ether material.

5. Apparatus as set forth in claim 2 wherein said first trapping means is of the normal phase type.

6. Apparatus as set forth in claim 5 wherein said second trapping means contains polyphenoxy ether material.

7. Apparatus as set forth in claim 2 wherein said first trapping means and said second trapping means contain material of the reverse bonded phase type.

8. Apparatus as set forth in claim 2 wherein said first trapping means and said second contain material of the normal phase type.

9. Apparatus as set forth in claim 2 wherein said first trapping means contains silica.

10. Apparatus as set forth in claim 2 wherein said first trapping means contains alumina.

11. Apparatus as set forth in claim 2 wherein said first trapping means contains charcoal.

12. Apparatus for concentrating solutes contained in a liquid solvent other than supercritical fluid and conveying them to chromatographic detection means, comprising:

trapping means for adsorbing and accumulating solutes from the liquid solvent when it passes therethrough, means for causing the liquid solvent, when present, to pass through said trapping means and out to waste, supercritical fluid chromatographic apparatus having a separation column, and means for causing supercritical fluid to pass through said trapping means and to the separation column of said chromatographic apparatus after the solutes have been accumulated in said trapping means.

13. In a chromatographic system, a method for deriving an amount of a solute that is above the minimum detectable level for the detector involved from a solvent other than a supercritical fluid in which the amount of solute contained in the largest sample volume of the solvent that can be injected is less than the minimum detectable level for the detector, the said method comprising:
  passing solvent through a first trapping means until the amount of solute accumulated therein is greater than the minimum detectable level,
  passing supercritical fluid through said first trapping means so as to adsorb at least a portion of the solute and then into a second trapping means, and
  reducing the solubility parameter of the supercritical fluid in said second trapping means so that an amount of the solute at least equal to the minimum detectable level is left in the second trapping means.

14. Apparatus for deriving an amount of solute that is above a given minimum detectable level for a given detector from a solvent in which the amount of solute contained in the largest sample volume of the solvent that can be used is less than the minimum detectable level for the detector, the said apparatus comprising:
  a first trapping means,
  means for causing solvent to pass through said first trapping means until the amount of solute contained therein exceeds the minimum detectable level,
  a second trapping means,
  a source of supercritical fluid and means for causing it to pass through said first trapping means and into said second trapping means, said second trapping means being such as to reduce the density of supercritical fluid entering it so as to reduce its solubility parameter.

15. Apparatus as set forth in claim 14 wherein said first trapping means is of the reverse phase type.

16. Apparatus as set forth in claim 15 wherein said second trapping means contains polyphenoxy ether material.

17. Apparatus as set forth in claim 14 wherein said first trapping means is of the normal phase type.

18. Apparatus as set forth in claim 17 wherein said second trapping means contains polyphenoxy ether material.

19. Apparatus as set forth in claim 14 wherein said first trapping means and said second trapping means contain material of the reverse bonded phase type.

20. Apparatus as set forth in claim 14 wherein said first trapping means and said second trapping means contain material of the normal phase type.

21. Apparatus as set forth in claim 14 wherein said first trapping means contains silica.

22. Apparatus as set forth in claim 14 wherein said first trapping means contains alumina.

23. Apparatus as set forth in claim 14 wherein said first trapping means contains charcoal.

24. Apparatus as set forth in claim 14 wherein said first trapping means is an HPLC column and said second trapping means contains polyphenoxyether polymer.

* * * * *